US005827677A

United States Patent [19]

Rousseau et al.

[11] Patent Number: 5,827,677
[45] Date of Patent: Oct. 27, 1998

[54] METHOD AND DEVICE FOR SPECIFICALLY DETECTING MYOGLOBIN USING A NON-DISCRIMINATING PEROXIDASE SENSITIVE ASSAY

[75] Inventors: Francois Rousseau, Ste-Foy; Jean-Claude Forest, Charlesbourg; Wiener Audouin, Levis, all of Canada

[73] Assignee: Universal Lavel, Quebec, Canada

[21] Appl. No.: 593,123

[22] Filed: Feb. 1, 1996

[51] Int. Cl.⁶ .................................................. C12Q 1/28
[52] U.S. Cl. .............................................. 435/28; 435/25
[58] Field of Search ........................... 435/25, 28; 424/4

[56] References Cited

U.S. PATENT DOCUMENTS

| | | | |
|---|---|---|---|
| 3,853,471 | 12/1974 | Rittersdorf et al. | 435/28 |
| 3,853,472 | 12/1974 | Rittersdorf et al. | 435/28 |
| 3,917,452 | 11/1975 | Rittersdorf et al. | 435/28 |
| 4,148,611 | 4/1979 | Nand et al. | 435/28 |
| 4,189,304 | 2/1980 | Adams, Jr. et al. | 435/28 |
| 4,481,295 | 11/1984 | Habenstein | 436/66 |
| 4,556,640 | 12/1985 | Gantzer | 436/66 |
| 5,081,040 | 1/1992 | Patel et al. | 436/66 |
| 5,318,894 | 6/1994 | Pugia | 435/28 |
| 5,362,633 | 11/1994 | Pugia | 435/28 |

FOREIGN PATENT DOCUMENTS

| | | |
|---|---|---|
| 2038603 | 2/1972 | Germany . |
| 1302162 | 12/1989 | Japan . |
| 3220455 | 9/1991 | Japan . |

OTHER PUBLICATIONS

Robitaile et al. (1995), Clinical Chemistry, vol. 41, No. 2, pp. 320–321, "Rapid Ultrafltration Method for Detecting Myocylobinuria".

Theil (1968), the Americal Journal of Clincal Pathology, vol. 49, No. 2, PP. 1990–195, "Seperation and Identification of Myoglobin and Hemoglobin".

Kelner et al (1985), Clinical Chemistry, vol. 31, No. 1, pp. 112–114, "Rapid Separation and Identification of myoglobin and Hemolobin in Urine by centrifugation through a Microconcentrator Membrane.".

Dox et al (1993) the Harper Collins Illustrated Medical Dictionary, pp. 154 and 199–200.

Robitaille et al. (1995). *Clinical Chemistry* 41(2): 320–321.

*Primary Examiner*—Gary E. Hollinden
*Assistant Examiner*—Dameron Jones
*Attorney, Agent, or Firm*—Merchant, Gould, Smith, Edell, Welter & Schmidt

[57] ABSTRACT

A method and device for detecting myoglobin amongst other mammalian peroxidatively active substances like hemoglobin is disclosed. Since the existing peroxidase-sensitive components do not discriminate between myoglobin and hemoglobin, the present method and device provide discrimination by including a filtration step or component which separates myoglobin from hemoglobin on the basis of their difference in molecular weights. The present method and device offer a quick and easy detection of myoglobin, especially in urine, and may conveniently use existing reagents and apparatus.

12 Claims, No Drawings

METHOD AND DEVICE FOR SPECIFICALLY DETECTING MYOGLOBIN USING A NON-DISCRIMINATING PEROXIDASE SENSITIVE ASSAY

FIELD OF THE INVENTION

This invention relates to a method of determining the presence or amount of myoglobin amongst other peroxidatively active substances like hemoglobin.

BACKGROUND OF THE INVENTION

Myoglobin is the $O_2$-binding protein of striated (cardiac and skeletal) muscle. Unlike hemoglobin (Hb), myoglobin exists only as a monomer (molecular mass~16 kDa). Myoglobinuria may be secondary to: (a) important crush injuries, severe exercise, seizures, muscular ischemia; (b) diminished energy production (hypokalemia, hypophosphatemia), (c) toxic substances (alcohol overdose, phencyclidine, carbon monoxide), and (d) infections (e.g., Legionnaires disease, influenza). Thus, myoglobinuria testing is often requested in emergency situations. In the past, myoglobin has been separated from Hb by molecular sieve chromatography (1) or centrifugation through a microconcentrator membrane (2) and identified spectrophotometrically. Latex agglutination can also be used, but this method is expensive and requires an experienced technologist to perform the analysis and to interpret the results reproducibly.

Recently, the Japanese patent application JP 1,302,162 described a Specific monoclonal antibody directed against myoglobin. This antibody is to be used in classical immunological assays. It could also be used in an antibody sensitized latex reagent.

Another Japanese patent application JP 3,220,455 describes an immunoassay of hemoglobin in urine by contacting a filtered urine with a known anti-hemoglobin antibody-sensitized latex reagent. Even though myoglobin may be in certain circumstances separated during the filtration step, it remains that no specific interest is paid to this particular molecule and even it it was recovered, it would still be measured by a latex agglutination test.

Compositions, methods and devices for detecting peroxidatively active substances like myoglobin and hemoglobin already exist (U.S. Pat. No. 4,148,611; 3,917,452; 3,853,471; 3,853,472 and U.S. Pat. No. Des. 2,038,603). More particularly, the peroxidase-sensitive dipstick sold under the trademark CHEMSTRIP™ by Boehringer-Mannheim GmbH is currently used in clinical laboratories. Although very convenient and easy to use comparatively to a latex agglutination test, these technologies do not discriminate between myoglobin and hemoglobin.

There is therefore a need for a simple and fast method for specifically determining the presence or amount of myoglobin in a test sample, which would be an advantageous alternative to an immunoassay using a specific anti-myoglobin antibody.

STATEMENT OF THE INVENTION

Here we propose a simple and quick method based on a peroxidase sensitive assay, but specifically directed to the measurement of myoglobin.

An object of the present invention is to provide a method for specifically determining the presence or amount of myoglobin amongst other mammalian peroxidatively active substances, particularly hemoglobin, in a test sample comprising the steps of:

a) separating myoglobin from said other mammalian peroxidatively active substances on the basis of their difference on molecular weights;

b) contacting said separated myoglobin with a detector composition signalling the peroxidase activity of mammalian peroxidatively active substances; and d) detecting a signal as an indication of the presence or amount of myoglobin in said test sample.

In the above method, steps a) and b) can be substantially simultaneous when this method makes use of a device comprising a cell containing the detector composition onto which is superimposed a filter membrane. The Chemtrip™ device, for example, can be easily modified to contain a cell topped or surrounded by a filter membrane. Such a process would eliminate an ultrafiltration step using an equipment like a Centricon™ apparatus.

The filter membrane having a molecular weight cutoff value comprised between about 20 kDa and about 50 kDa, more particularly about 30 kDa, is used in the present method.

The existing methods and devices such as the CHEMSTRIP™ device lead to a scale evaluation of the density of erythrocytes present in said test sample as an indication of the presence of mammalian peroxidatively active substances. The above method allows the user to detect myoglobin within the same scale.

After being contacted with a urine sample, the CHEMSTRIP™ device is capable of reading a scale ranging from about 0 to about $250 \times 10^6$ erythrocytes per liter of said test sample. The scale is stepwise and divided as follows: $\leq 10^7$, $25 \times 10^6$, $50 \times 10^6$, $150 \times 10^6$, $250 \times 10^6$.

In the present method, myoglobin is positively detected when a scale value of $\geq 10^7$ erythrocytes per liter of test sample is detected.

A density of erythrocytes corresponding to a concentration of myoglobin as low as about 300 $\mu$g per liter of test sample is detectable with the above method.

It is another object of the invention to provide a test strip device for measuring the presence or amount of myoglobin in a test sample comprising:

a detecting cell which components signal a peroxidase activity in said test sample, said detecting cell having at least one side which is permeable to aqueous solutions;

a filter membrane having a molecular weight cutoff value comprised between about 20 kDa to about 50 kDa, which filter membrane covers said at least one side of said detecting cell which is permeable to aqueous solutions; and a support strip member which is impervious to aqueous solutions, which support member is sealed to said detecting cell and filter membrane.

In a specific embodiment of the invention, the cutoff value of the filter membrane is of about 30 kDa, It is another object of the invention to provide a test device for measuring the presence or amount of myoglobin in a test sample and which is not necessarily a strip device comprising:

a detecting cell member which components signal a peroxidase activity in said test sample, said detecting cell member comprising a site which is permeable to aqueous solutions;

a filter member having a molecular weight cutoff value comprised between about 20 kDa to about 50 kDa, which filter member covers said permeable site, so as to preclude a direct contact of said test sample with said detecting cell member components.

In a specific embodiment of the invention, the cutoff value of the membrane is about 30 kDa.

In another specific embodiment said test sample is pushed through said filter member by pushing means, such as a syringe, which is connected to the filter membrane or to the detecting cell member by connecting means.

In another specific embodiment, the detecting cell member comprises an aperture at a site different from the permeable site which is adaptable to pumping means by connecting means, whereby said teat sample is contacted with said filter member and pumped into said detecting cell member, the assembly being such that it precludes the direct contact of the test sample with the detecting cell.

DESCRIPTION OF THE INVENTION

The present invention will be further described hereinbelow by way of the following specific examples whose purpose is not to limit the scope of the invention.

EXAMPLE 1

1) A urine specimen has been centrifuged for 5 minutes 1500 g.

2) The supernatant has been tested with a peroxidase-sensitive dipstick (e.g., CHEMSTRIP 10A; Boehringer Mannheim Canada, Laval, PQ, Canada) used for hemoglobinuria, and the results were read.

3) When the Hb reaction in the unfiltered urine indicated an $\leq 10^7$ ery/L, "absence of myoglobin in significant quantity" was reported, if the reaction indicated $\geq 25 \times 10^6$ ery/L [+], the sample was allowed to proceed to step 4.

4) 1 mL of urine was added to the sample reservoir of a Centricon-30™ concentrator (Amican, Beverly, Mass.; 30-kDa cutoff) and centrifuged (10 min, 4000 g).

5) The peroxidase test (Hb dipstick) was performed again on the filtrate, and thee results were read.

6) If the Hb reaction was negative, "myoglobin not detectable" was reported, if the reaction indicated $\geq 10^7$ ery/L, "presence of myoglobin" was reported.

We compared the performance of this test with that of a latex agglutination kit (Rapitex-Myoglobin; Behring, Montreal, Canada), modified for urine analysis. We analysed urine specimens to which various concentrations of purified equine myoglobin (Sigma, St. Louis, Mo.) had been added and samples from 10 patients having various degrees of rhabdomyolysis. In the absence of hematuria/hemoglobinuria, a dipstick result of $25 \times 10^6$ ery/L [+] before ultrafiltration corresponded to a concentration of equine myoglobin of ~300 µg/L. The Rapitex method gave a definite positive result with a urine specimen containing 100 µg/L myoglobin. A myoglobin-negative urine sample with lysed red blood cells added to the level of visible hematuria (reddish color) gave a $\geq 250 \times 10^6$ ery/L [++++] reading on direct analysis with tie dipstick but a negative result for the ultrafiltrate. All 10 patients with positive Rapitex results also tested positive with the dipstick/ultrafiltration method. Filtrates from all urine specimens to which purified equine myoglobin was added before filtration gave dipstick results one [+] sign less than they did before ultrafiltration. This suggests that a small percentage of myoglobin is retained by the membrane. Multiple analyses made on the same specimens (even after frozen storage of 3 months) gave identical results.

We find the proposed method easier to perform, cheaper, less time-consuming and less labor-intensive than the latex agglutination methods. Complete analysis takes about 20 min. The analytical sensitivity is slightly better with the Rapitex than with the method described here but the clinical importance of this difference is not apparent. Finally, this method appears to be reproducible and is easier to interpret than the latex agglutination methods.

EXAMPLE 2

Since the results obtained in Example 1 show that a filtration step is sufficient to convert an existing test non-specific to myoglobin to a specific one, the filtration step may take different forms:

a centrifugation step using a membrane whose molecular cutoff value is comprised between about 20 kDa to about 50 kDa; Centricon apparatus and Amicon membranes of about 30 kDa cutoff value are currently and conveniently used to this effect;

a filtration step with the same cutoff values performed by way of a filter cartridge, which could be easily adapted to the tip of pipette or of a syringe; or the addition of a filter membrane of the same cutoff values on the detecting cell of existing devices.

EXAMPLE 3

A new device similar to the CHEMSTRIP™ or a test strip device comprising other peroxidase-sensitive components capable of selectively recognizing mammalian peroxidatively active substances can be therefore designed to specifically measure myoglobin in a test sample alone or in combination with other cells capable of detecting other test sample components. This particular device would be advantageous since it could be simply dipped in a test sample and results can be read with the existing equipment for reading Hb results.

A test strip device can be easily derived for the determination of the presence or amount of myoglobin in a test sample. Since it is necessary to allow the passage of myoglobin through a filter membrane while precluding the passage of hemoglobin, a strip device resembling the CHEMSTRIP™ device can be modified to comprise a Hb cell covered by a filter membrane. Normally, a strip device should comprise a support strip which is impervious to aqueous solutions onto which a peroxidase-sensitive detecting cell which is topped or surrounded by a filter membrane is fixed in such a way that there is no undesired passage of hemoglobin through the cell to reach the detecting components thereof. The backside of the cell and/or the membrane would be imperviously sealed to the strip support. The filter membrane is added to cover the detecting cell on at least the front side, if one assumes that the lateral sides of the detecting cell are imperviously sealed. Otherwise, the filter membrane can also cover the lateral sides, and eventually the back side of the cell. The filter membrane and cell assembly is imperviously sealed to the strip support except for the permeable filter/cell section.

The so constructed strip device is simply dipped in a test sample, like a urine sample, for a time sufficient to allow diffusion of myoglobin through the pores of the filter membrane. In order to perform a quick assay, the porosity of the filter membrane should be such that it does not impede a rapid diffusion of myoglobin through it. The sensitivity of the reagents composing the detecting cell should be such that a low concentration of myoglobin could be easily detected. Membranes of a molecular weight cutoff value of 30 kDa are currently available and are useful in the present device, but filter membranes of higher cutoff values may be designed and used to accelerate the diffusion of myoglobin towards the cell components. In order to preclude the diffusion of hemoglobin which has a molecular weight of more than 60 kDa, a porosity at as high as about 50 kDa could be advantageously used.

The strip device could be also laid down, the detecting cell facing up, and a small volume of urine would be deposited directly on the filter membrane. Therefore, myoglobin could be driven through the membrane by diffusion and gravitational force.

The diffusion of myoglobin through the filter membrane of the device could be also accelerated by using the same strip device or by designing a different type of device which would not have necessarily a strip shape. For example, a device having a detecting cell member having a permeable site topped or surrounded by a filter membrane could also contain connecting means to receive remote pushing means such as a syringe. A test sample would then be pushed towards the filter and the cell components. Alternatively, an aperture can be made in the detecting cell member at a site different from the permeable site, which aperture is connectable to remote pumping means such as a syringe, through connecting means. A test sample would then by pumped towards the cell components while avoiding a direct contact of the test sample with the latter.

The devices are adapted for the method of Examples 1 and 2, in which the steps of separating myoglobin and other mammalian peroxidatively active substances and of contacting the separated myoglobin with the detecting cell components do not require separate handling steps. These two steps would therefore become substantially simultaneous and would not require an ultrafiltration equipment such as a Centricon apparatus.

The invention has been described hereinabove, and it will become apparent to a skilled reader that variations thereof can be made without departing from the above teachings. These variations are under the scope of the invention.

What is claimed is:

1. A method for specifically determining the presence or amount of myoglobin amongst other mammalian peroxidatively active substances in a test sample comprising the steps of:

(a) separating myoglobin from said other mammalian peroxidatively active substances on the basis of their difference on molecular weights;

b) contacting said separated myoglobin with a detector composition which leads to a scale evaluation of the density of erythrocytes population in said sample; and (c) detecting the presence or amount of erythrocytes evaluated with said scale as an indication of the presence or amount of myoglobin in said test sample.

2. A method according to claim 1, wherein steps a) and b) are substantially simultaneous.

3. A method according to claim 1, wherein step a) is performed on a filter membrane having a molecular weight cutoff value comprised between about 20 kDa and about 50 kDa.

4. A method according to claim 2, wherein step a) is performed on a filter membrane having a molecular weight cutoff value comprised between about 20 kDa and about 50 kDa.

5. A method according to claim 3, wherein said cutoff value is of about 30 kDa.

6. A method according to claim 4, wherein said cutoff value is of about 30 kDa.

7. A method according to claim 1, wherein said test sample is a urine sample.

8. A method according to claim 2, wherein said test sample is a urine sample.

9. A method according to claim 5, wherein said test sample is a urine sample.

10. A method according to claim 9, wherein said scale comprises values from about 0 to about $250 \times 10^6$ erythrocytes per liter of said test sample.

11. A method according to claim 10, wherein myoglobin is positively detected when a scale value equal to or greater than about $10^7$ erythrocytes per liter of test sample is detected.

12. A method according to claim 10, wherein the density of erythrocyte population corresponding to a concentration of myoglobin of at least about 100 µg per liter of test sample is positively detectable.

* * * * *

UNITED STATES PATENT AND TRADEMARK OFFICE
CERTIFICATE OF CORRECTION

PATENT NO. : 5,827,677

DATED : OCTOBER 27, 1998

INVENTOR(S) : ROSSEAU ET AL.

It is certified that error appears in the above-identified patent and that said Letters Patent is hereby corrected as shown below:

On the cover page, [73] Assignee: "Universal Lavel" should read --Université Laval--.

On the cover page [56] References Cited, Other Publications: In the "Theil (1968)" reference, "PP. 1990-195" should read --pp. 190-195--.

On the cover page [56] References Cited, Other Publications: In the "Kelner et al (1985)" reference, "myoglobin" should read --Myoglobin-- and "centrifugation" should read --Centrifugation--.

At column 2, line 7, "d)" should read --c)--.

At column 3, lines 22-23, "5 minutes 1500g." should read --5 minutes at 1500 g.--

At column 3, line 36, "thee" should read --the--.

Signed and Sealed this

Eighth Day of June, 1999

*Attest:*

Q. TODD DICKINSON

*Attesting Officer*     *Acting Commissioner of Patents and Trademarks*